(12) United States Patent
Jacobson et al.

(10) Patent No.: US 9,187,777 B2
(45) Date of Patent: Nov. 17, 2015

(54) METHODS AND DEVICES FOR IN SITU NUCLEIC ACID SYNTHESIS

(75) Inventors: Joseph Jacobson, Newton, MA (US); Senthil Ramu, Cambridge, MA (US); Daniel Schindler, Newton, MA (US)

(73) Assignee: Gen9, Inc., Cambridge, MA (US)

( * ) Notice: Subject to any disclaimer, the term of this patent is extended or adjusted under 35 U.S.C. 154(b) by 185 days.

(21) Appl. No.: 13/700,291

(22) PCT Filed: May 26, 2011

(86) PCT No.: PCT/US2011/038079
§ 371 (c)(1),
(2), (4) Date: Jul. 12, 2013

(87) PCT Pub. No.: WO2011/150168
PCT Pub. Date: Dec. 1, 2011

(65) Prior Publication Data
US 2013/0309725 A1    Nov. 21, 2013

Related U.S. Application Data

(60) Provisional application No. 61/349,585, filed on May 28, 2010.

(51) Int. Cl.
*C12Q 1/68* (2006.01)
*C12P 19/34* (2006.01)
*C12N 15/10* (2006.01)
*C12N 15/66* (2006.01)

(52) U.S. Cl.
CPC ............. *C12P 19/34* (2013.01); *C12N 15/1093* (2013.01); *C12N 15/66* (2013.01)

(58) Field of Classification Search
CPC ...... C12P 19/34; C12N 15/1093; C12N 15/66
See application file for complete search history.

(56) References Cited

U.S. PATENT DOCUMENTS

| | | |
|---|---|---|
| 4,652,639 A | 3/1987 | Stabinsky |
| 5,132,215 A | 7/1992 | Jayaraman et al. |
| 5,143,854 A | 9/1992 | Pirrung et al. |
| 5,288,514 A | 2/1994 | Ellman |
| 5,384,261 A | 1/1995 | Winkler et al. |
| 5,510,270 A | 4/1996 | Fodor et al. |

(Continued)

FOREIGN PATENT DOCUMENTS

| | | |
|---|---|---|
| EP | 1 205 548 | 5/2002 |
| WO | WO 99/429813 | 8/1999 |

(Continued)

OTHER PUBLICATIONS

Mir, et al., "Sequencing by Cyclic Ligation and Cleavage (CycLiC) dirctly on a microarray captured template", Nucleic Acids Research, vol. 37, No. 1, (2009).

(Continued)

*Primary Examiner* — Young J Kim
(74) *Attorney, Agent, or Firm* — Greenberg Traurig, LLP; Natalie Salem; Fang Xie

(57) ABSTRACT

Disclosed are compositions, methods and devices for the in situ synthesis of nucleic acids. In an exemplary embodiment, a support-bound oligonucleotide is elongated by addition of one or more nucleotides by hybridization of a partially double-stranded oligonucleotide, ligation and removal of unwanted nucleotides.

26 Claims, 9 Drawing Sheets

(56) References Cited

U.S. PATENT DOCUMENTS

| | | |
|---|---|---|
| 5,527,681 A | 6/1996 | Holmes |
| 5,541,061 A | 7/1996 | Fodor et al. |
| 5,639,603 A | 6/1997 | Dower et al. |
| 5,700,637 A | 12/1997 | Southern |
| 5,700,642 A | 12/1997 | Monforte et al. |
| 5,739,386 A | 4/1998 | Holmes |
| 5,770,358 A | 6/1998 | Dower et al. |
| 5,830,655 A | 11/1998 | Monforte et al. |
| 5,866,363 A | 2/1999 | Pieczenik |
| 5,942,609 A | 8/1999 | Hunkapiller et al. |
| 6,322,971 B1 | 11/2001 | Chetverin et al. |
| 6,375,903 B1 | 4/2002 | Cerrina et al. |
| 6,376,246 B1 | 4/2002 | Crameri et al. |
| 6,479,262 B1 | 11/2002 | Delagrave |
| 6,586,211 B1 | 7/2003 | Stahler et al. |
| 6,635,453 B2 | 10/2003 | Delagrave et al. |
| 6,664,112 B2 | 12/2003 | Mulligan et al. |
| 6,670,127 B2 | 12/2003 | Evans |
| 6,800,439 B1 | 10/2004 | McGall et al. |
| 6,824,866 B1 | 11/2004 | Glazer et al. |
| 6,830,890 B2 | 12/2004 | Lockhart et al. |
| 6,833,450 B1 | 12/2004 | McGall et al. |
| 7,090,979 B2 | 8/2006 | Mariella, Jr. et al. |
| 7,164,992 B1 | 1/2007 | Mulligan et al. |
| 7,482,119 B2 | 1/2009 | Parker et al. |
| 7,544,793 B2 | 6/2009 | Gao et al. |
| 7,563,600 B2 | 7/2009 | Oleinikov |
| 7,695,906 B2 | 4/2010 | Schatz et al. |
| 8,053,191 B2 | 11/2011 | Blake |
| 8,716,467 B2 | 5/2014 | Jacobson |
| 8,808,986 B2 | 8/2014 | Jacobson et al. |
| 2002/0081582 A1 | 6/2002 | Gao et al. |
| 2003/0068633 A1 | 4/2003 | Belshaw et al. |
| 2003/0186226 A1 | 10/2003 | Brennan |
| 2003/0198948 A1 | 10/2003 | Stahler et al. |
| 2003/0215837 A1 | 11/2003 | Frey et al. |
| 2004/0106728 A1 | 6/2004 | McGall et al. |
| 2009/0298133 A1 | 12/2009 | Schatz et al. |
| 2012/0220497 A1 | 8/2012 | Jacobson et al. |
| 2012/0283140 A1 | 11/2012 | Chu |
| 2012/0322681 A1 | 12/2012 | Kung |
| 2013/0059296 A1 | 3/2013 | Jacobson et al. |
| 2013/0281308 A1 | 10/2013 | Kung et al. |
| 2013/0296194 A1 | 11/2013 | Jacobson et al. |
| 2013/0309725 A1 | 11/2013 | Jacobson et al. |
| 2014/0141982 A1 | 5/2014 | Jacobson et al. |

FOREIGN PATENT DOCUMENTS

| | | |
|---|---|---|
| WO | 00075368 | 12/2000 |
| WO | WO 02/24597 | 3/2002 |
| WO | WO 03/40410 | 5/2003 |
| WO | WO 03/46223 | 6/2003 |
| WO | WO 03/64026 | 8/2003 |
| WO | WO 03/064027 | 8/2003 |
| WO | WO 03/064699 | 8/2003 |
| WO | WO 03/065038 | 8/2003 |
| WO | WO 03/066212 | 8/2003 |
| WO | WO 03/100012 | 12/2003 |
| WO | WO 2004/029586 | 4/2004 |
| WO | WO 2004/031351 | 4/2004 |
| WO | WO 2004/031399 | 4/2004 |
| WO | 2005/071077 | 8/2005 |
| WO | 2005071077 | 8/2005 |
| WO | 2010/025310 | 3/2010 |
| WO | 2011066186 | 6/2011 |
| WO | 2011085075 | 7/2011 |
| WO | 2011143556 | 11/2011 |
| WO | 2014004393 | 1/2014 |
| WO | 2014151696 | 9/2014 |
| WO | 2014160004 | 10/2014 |
| WO | 2014160059 | 10/2014 |

OTHER PUBLICATIONS

International Search Report of PCT/US2011/038079 mailed Oct. 27, 2011.
Blanchard, A., "Synthetic DNA Arrays," Genetic Engineering, 20:111-123, Plenum Press, (1998).
Duggan et al., "Expression profiling using cDNA microarrays," Nat. Genet., 21: 10-14 (1999).
Fodor et al. "Light-directed, spatially addressable parallel chemical synthesis," Science. 251(4995): 767-773 (1991).
McGall et al., "Light-directed synthesis of high-density oligonucleotide arrays using semiconductor photoresists," PNAS. 93(24): 13555-13560 (1996).
Pon, R., "Solid-phase supports for oligonucleotide synthesis," Methods Mol. Biol. 20: 465-496 (1993).
Stekel, D., "Microarrays: Making Them and Using Them in Microarray Bioinformatics," Cambridge University Press. 1-10 (2003).
Verma et al., "Modified oligonucleotides: Synthesis and Strategy for Users," Annu. Rev. Biochem. 67: 99-134 (1998).
Zhou X. et al. "Microfluidic PicoArray synthesis of oligodeoxynucleotides and simultaneous assembling of multiple DNA sequences" Nucleic Acids Research. 32(18): 5409-5417 (2004).

METHODS AND DEVICES FOR IN SITU NUCLEIC ACID SYNTHESIS

RELATED APPLICATIONS

This application is a National Stage application of International Application No. PCT/US2011/038079, filed May 26, 2011, which claims the benefit of and priority to U.S. Provisional Application Ser. No. 61/349,585, filed May 28, 2010, the entire contents of each of the foregoing applications are herein incorporated by reference in their entirety.

FIELD OF THE INVENTION

The present invention relates to nucleic acid synthesis and more particularly to in situ synthesis of nucleic acids such as oligonucleotides.

BACKGROUND

Synthetic biopolymers such as oligonucleotides play a pivotal role in many fields such as molecular biology, forensic science, and medical diagnostics. Oligonucleotides, in particular, have become indispensable tools in modern biotechnology. Oligonucleotides are being used in a wide variety of techniques, ranging from diagnostic probing methods, PCR, antisense inhibition of gene expression to nucleic acid assembly. This widespread use of oligonucleotides has led to an increasing demand for rapid, inexpensive and efficient methods for synthesizing oligonucleotides.

Nucleic acid arrays such as DNA and RNA arrays are useful in a variety of different fields such as diagnostics (for example single polymorphism detection), genomics (for example genomic DNA purification, differential gene expression analysis) and synthetic biology (for example, gene synthesis).

SUMMARY

Aspects of the technology provided herein relate to devices, methods and compositions for synthesizing nucleic acids (e.g. polynucleotides or oligonucleotides) having a predefined sequence. Aspects of the invention relate to the devices and methods for the synthesis of a plurality of nucleic acids and/or libraries of nucleic acids on a solid support. In one aspect, a device for synthesizing a nucleic acid having a predetermined sequence is provided.

Aspects of the invention relate to a method for synthesizing a nucleic acid having a predefined sequence, the method comprising: a) providing a support comprising an anchor oligonucleotide at a first feature; b) hybridizing a partially double-stranded first oligonucleotide to the anchor oligonucleotide wherein the first oligonucleotide comprises a 5' overhang and ligatable predetermined addition nucleotide at a 3' end of the double-stranded portion; c) ligating the first oligonucleotide to the anchor oligonucleotide thereby generating a first ligation product; and d) removing unwanted nucleotides from the first ligation product thereby generating a first elongated product comprising the predetermined terminal nucleotide. Steps b) c) and d) may be repeated to synthesize the nucleic acids having the predefined sequence. In some embodiments, the anchor oligonucleotide is support-bound. Yet, in other embodiments, the anchor oligonucleotide is in solution within a droplet. In some embodiments, the support comprises a plurality of features, each feature comprising a plurality of single-stranded anchor oligonucleotides.

In some embodiments, the partially double-stranded oligonucleotides comprises a double-stranded portion and a single-stranded 5' overhang, wherein the single-stranded overhang comprises degenerate bases. In some embodiments, the partially double-stranded oligonucleotides are generated by hybridizing a first construction oligonucleotide comprising at its 5' end, a predefined sequence, and at its 3' end, the predetermined ligatable addition nucleotide, to a longer oligonucleotide comprising from its 5' end to its 3' end: a single-stranded overhang, a nucleotide complementary to the predetermined addition nucleotide, and at its 3' end a sequence complementary to the 5' end predefined sequence of the first construction oligonucleotide. The single-stranded overhang may be complementary to the 5' end of the anchor oligonucleotide.

In some embodiments, the nucleotide upstream of the predetermined addition nucleotide on the first construction oligonucleotide is a RNA base. In some embodiments, the step of removing comprises cleaving the first ligation product using a RNase.

In other embodiments, the double-stranded portion of the partially double-stranded oligonucleotide comprises a restriction endonuclease binding site. The restriction endonuclease may be a type II S endonuclease. In some embodiments, removing nucleotides from the ligation product comprises cleaving the ligation product with a restriction enzyme. The cleavage provides an elongated product comprising the predetermined nucleotide addition. In some embodiments, nucleotides are melted off and washed off from the elongated product.

In some embodiments, the partially double-stranded oligonucleotides comprise a detectable label. The label is preferably a fluorescent label. In some embodiments, the methods further comprise analyzing the hybridization step and/or the ligation step, wherein the presence of the detectable label is indicative of the completion of the step(s). In some embodiments, the method comprises analyzing the removal step wherein the absence of detectable label is indicative of the completion of the step. The steps of analyzing are preferably performed using an imaging system such as a CCD.

In some embodiments, the partially double-stranded first oligonucleotide is deposited at the first location or feature using an ink jet device. In some embodiments, a plurality of partially double-stranded oligonucleotides are provided at a plurality of different features. The plurality of partially double-stranded oligonucleotides preferably comprises a 5' single-stranded overhang, a predetermined addition nucleotide and a double-stranded portion and wherein the double-stranded portion is identical within the plurality of oligonucleotides. The plurality of oligonucleotides may differ only with at least one desired nucleotide addition such as A. T, G or C. In some embodiments, the first elongated product comprises one or more predetermined addition nucleotides.

Another aspect of the invention relates to a composition for synthesizing a plurality of nucleic acids on a surface of a solid support, the composition comprising a plurality of partially double-stranded oligonucleotide wherein the plurality of partially double-stranded oligonucleotide comprises a 5' single-stranded sequence and a double-stranded sequence comprising a predefined sequence and a predetermined ligatable nucleotide addition at a 3' end of the shorter strand of the double-stranded sequence, wherein the double-stranded sequence is identical within the plurality of oligonucleotides. In some embodiments, the double-stranded portion comprises a restriction enzyme binding site. In some embodiments, the shorter strand comprises at least one RNA base upstream of the predetermined addition nucleotide. In some embodiments, the 5' single-stranded sequence is a degenerate sequence.

The partially double-stranded Nucleotide addition construct NacC has the following sequence:
5' NNNNGGAGGAGC 3' (SEQ ID NO: 2)
3' CCTCCTCG 5'

Figure 7:
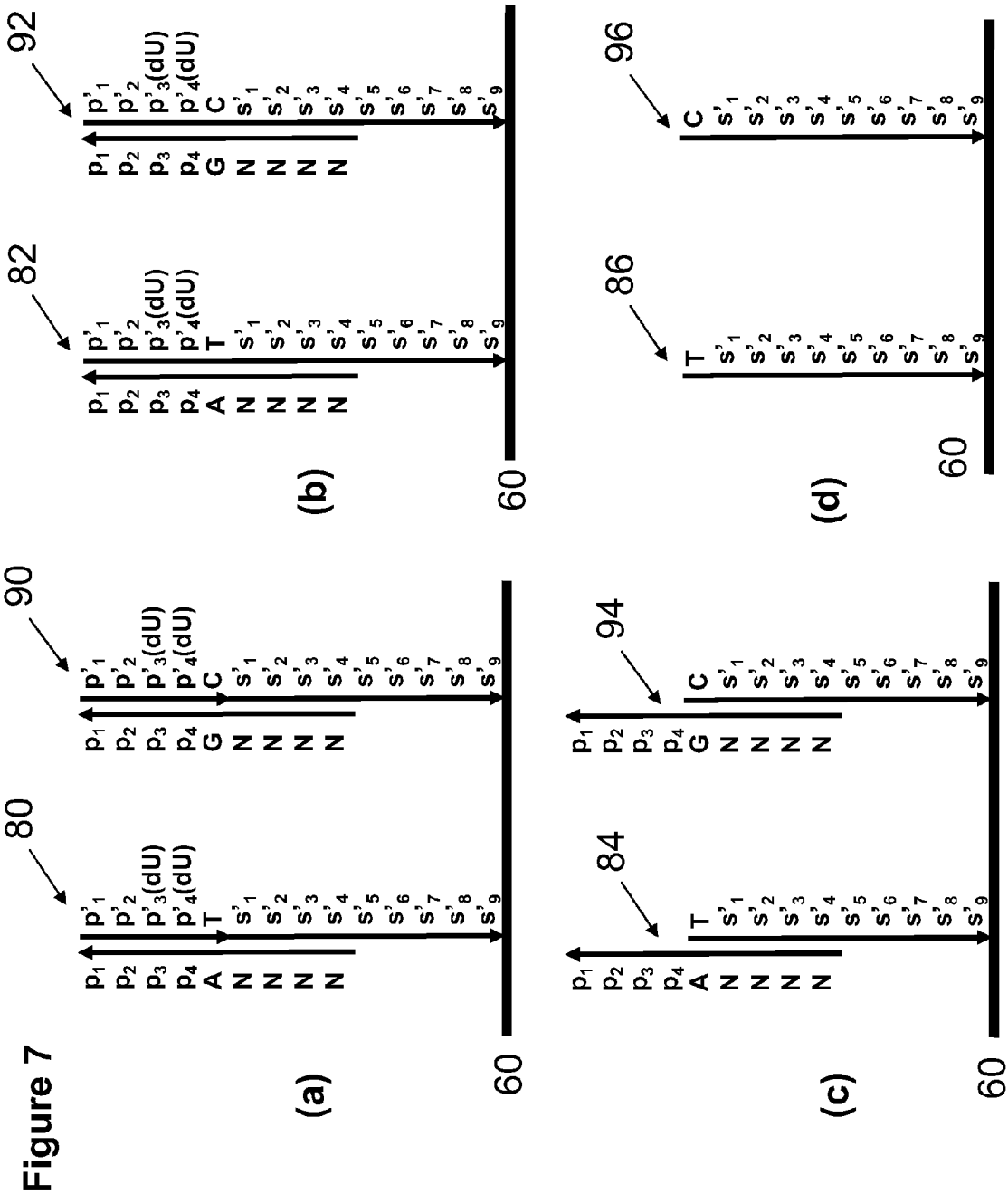

FIG. 7 is a non-limiting schematic illustration of the process of a single nucleotide addition to support-bound oligonucleotides by hybridization of nucleotide addition constructs to support-bound oligonucleotides followed by deoxy-uracil base excision.

Figure 8:
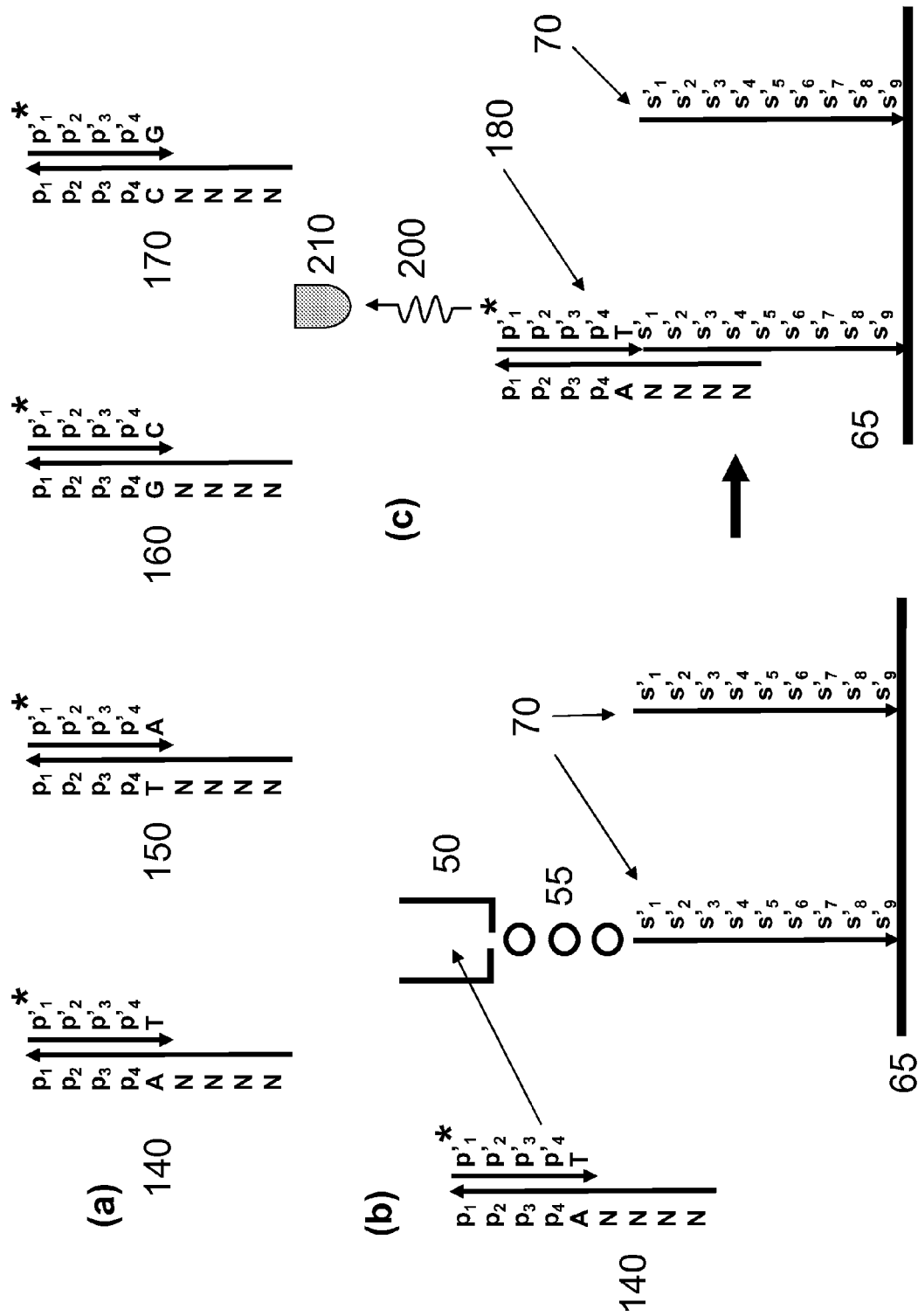

FIG. 8 is a non-limiting schematic illustration of real time or single molecule in-situ nucleic acid synthesis.

DETAILED DESCRIPTION OF THE INVENTION

Aspects of the invention relate to a device and/or methods for synthesizing a nucleic acids having a desired or predetermined sequence on a solid support. The device and methods described herein permits relatively inexpensive, rapid, and high fidelity construction of essentially any desired nucleic acid. Unless defined otherwise below, all technical and scientific terms used herein have the same meaning as commonly understood by one of ordinary skill in the art to which this disclosure belongs. Still, certain elements are defined herein for the sake of clarity. It must be noted that, as used in this specification and the appended claims, the singular forms "a", "an" and "the" include plural referents unless the context clearly dictates otherwise. Thus, for example, reference to "a polynucleotide" can include more than one polynucleotide.

Aspects of the invention relate to the synthesis of nucleic acids and more particularly to the in situ synthesis of nucleic acids on the surface of a solid support. Oligonucleotides or polynucleotides of any length can be produced by the devices and methods described herein. In some embodiments, methods are provided for generating high numbers of nucleic acids such a DNA, RNA or oligonucleotides. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to from an oligomer, a polymer or a compound composed of two or more members. The particular ordering of monomers within a polymer is referred to herein as the "sequence" of the polymer. The set of monomers includes but is not limited to example, the set of common L-amino acids, the set of D-amino acids, the set of synthetic and/or natural amino acids, the set of nucleotides and the set of pentoses and hexoses. Aspects of the invention described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

In some embodiments, the methods provided herein use oligonucleotides that are immobilized on a surface or substrate (e.g., support-bound oligonucleotides). As used herein the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single-stranded oligonucleotides are bound to the surface of the support or feature. As used herein the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support.

Various types of microarray manufacturing devices and technologies have been described e.g. combinatorial array, ink jetting, direct surface printing. There is a variety of methods known to synthesize such nucleic acid molecules having a predefined sequence. Oligonucleotide synthesis can be performed through massively parallel custom syntheses on microchips (Zhou et al. (2004) Nucleic Acids Res. 32:5409; Fodor et al. (1991) Science 251:767). Nucleic acid arrays are comprised of a surface to which are attached to a set of oligonucleotides of specific or predefined sequence, most typically in known location or address. Pre-synthesized oligonucleotides may be attached to the surface or a solid support or oligonucleotides may be synthesized in-situ. Given the difficulty of separately synthesizing and then attaching large numbers of different oligonucleotides to a surface, in-situ synthesized arrays are typically of significantly greater density that pre-synthesized oligonucleotides arrays, with spot densities currently up to several million. In order to create an in-situ synthesized array means are needed for directing the order of nucleotide addition to the various positions on a surface. Practically, all of these procedures rely on synthesis via chemical reactions such as phosphoramidite chemistry and/or rely on both acid labile and photolabile deprotection chemistries. For acid labile chemistries, the local acid condition may be varied by means which include the direct ink jet of an acid, the stamping of an acid or the electrochemical generation of an acid or photogneration of an acid. For photolabile chemistries the local optical condition may be varied by means of a steerable laser, photomask or DMD. Spurious chemical reactions cause random base errors in oligonucleotides. The techniques suffer from the requirement of running organic chemistries which are sensitive to moisture as well from dupurination errors which come from acid exposure or from bond cleavage errors which come from repeated UV exposure. Accordingly, there is a need in the art to provide for a method and devices for the in situ synthesis of pluralities of nucleic acids using a small number of biologically-based and enzymatic reagents.

In some embodiments, oligonucleotides are attached, spotted, immobilized, surface-bound, supported or synthesized on the discrete features of the surface or array. Oligonucleotides may be covalently attached to the surface or deposited on the surface. Arrays may be constructed, custom ordered or purchased from a commercial vendor (e.g., Agilent, Affymetrix, Nimblegen). Various methods of construction are well known in the art e.g., maskless array synthesizers, light directed methods utilizing masks, flow channel methods, spotting methods etc. In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence. Other methods for synthesizing construction and/or selection oligonucleotides include, for example, light-directed methods utilizing masks, flow channel methods, spotting methods, pin-based methods, and methods utilizing multiple supports. Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261. Additional methods applicable to synthesis of construction and/or selection oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized on multiple supports. One example is a bead based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g., ink jet). In some embodiments, oligonucleotides are spotted on a support using, for example, a mechanical wave actuated dispenser.

One aspect of the invention relates to compositions useful for the in situ synthesis of a plurality of oligonucleotides having a predefined sequence onto a support. Another aspect of the invention relates to a device for synthesizing a plurality of oligonucleotides having a predetermined sequence on a solid support. In some aspects of the invention, the compositions described herein are particularly useful for fabricating an addressable oligonucleotide array by in situ synthesis of oligonucleotides on a solid support. In one such embodiment, at each of the multiple different addresses on the support, the in situ synthesis steps may be repeated so as to form a support comprising a plurality of oligonucleotides (e.g. same or different oligonucleotide sequences) at one or more different addresses on the support. In some embodiments, the compositions of the invention are deposited as droplets at those addresses using, for example, a pulse-jet printing system. The oligonucleotides can be produced by disposing solutions on particular addressable positions in a specific order in an iterative process. As used herein, the term "predefined sequence" or "predetermined sequence" are used interchangeably and means that the sequence of the polymer is known and chosen before synthesis or assembly of the polymer. In particular, aspects of the invention are described herein primarily with regard to the preparation of nucleic acids molecules, the sequence of the oligonucleotide or polynucleotide being known and chosen before the synthesis or assembly of the nucleic acid molecules. In one embodiment, "oligonucleotides" are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Each oligonucleotide may be designed to have a different length.

In one aspect of the invention, a device for synthesizing a plurality of nucleic acids having a predetermined sequence is provided. The device can include a support having a plurality of features, each feature having a plurality of anchor oligonucleotides. In some embodiments, the plurality anchor oligonucleotides having a predefined sequence are immobilized at different discrete features of a solid support. In some embodiments, the anchor oligonucleotides are single-stranded. In some embodiments, the plurality of anchor oligonucleotide sequences may comprise degenerate sequences. In some embodiments, the anchor oligonucleotides are support-bound. In some embodiments, the device comprises a solid support having a plurality of spots or features, and each of the plurality of spots includes a plurality of support-bound oligonucleotides. In some embodiments, the anchor oligonucleotides are covalently linked through their 3' end to the solid support. Yet, in other embodiments the anchor oligonucleotides are covalently linked through their 5' end to the solid support.

In some embodiments, the anchor or support-bound oligonucleotides are immobilized through their 3' end. It should be appreciated that by 3' end, it is meant the sequence downstream to the 5' end and by 5' end it is meant the sequence upstream to the 3' end. For example, an oligonucleotide may be immobilized on the support via a nucleotide sequence (e.g., a degenerate binding sequence), a linker or spacer (e.g., a moiety that is not involved in hybridization). In some embodiments, the anchor oligonucleotide comprises a spacer or linker to separate the anchor oligonucleotide sequence from the support. Useful spacers or linkers include photocleavable linkers, or other traditional chemical linkers. In one embodiment, oligonucleotides may be attached to a solid support through a cleavable linkage moiety. For example, the solid support may be functionalized to provide cleavable linkers for covalent attachment to the oligonucleotides. The linker moiety may be of six or more atoms in length. Alternatively, the cleavable moiety may be within an oligonucleotide and may be introduced during in situ synthesis. A broad variety of cleavable moieties are available in the art of solid phase and microarray oligonucleotide synthesis (see e.g., Pon, R., Methods Mol. Biol. 20:465-496 (1993); Verma et al., Annu Rev. Biochem. 67:99-134 (1998); U.S. Pat. Nos. 5,739,386, 5,700,642 and 5,830,655; and U.S. Patent Publication Nos. 2003/0186226 and 2004/0106728). A suitable cleavable moiety may be selected to be compatible with the nature of the protecting group of the nucleoside bases, the choice of solid support, and/or the mode of reagent delivery, among others. In an exemplary embodiment, the oligonucleotides cleaved from the solid support contain a free 3'-OH end. Alternatively, the free 3'-OH end may also be obtained by chemical or enzymatic treatment, following the cleavage of oligonucleotides. The cleavable moiety may be removed under conditions which do not degrade the oligonucleotides. Preferably the linker may be cleaved using two approaches, either (a) simultaneously under the same conditions as the deprotection step or (b) subsequently utilizing a different condition or reagent for linker cleavage after the completion of the deprotection step.

In other embodiments, the anchor oligonucleotides are in solution. For example, the anchor oligonucleotides may be provided within a discrete volume such as a droplet or microdroplet at different discrete features. In some embodiments, discrete microvolumes of between about 0.5 μL and about 100 mL may be used. However, smaller or larger volumes may be used. In some embodiments, a mechanical wave actuated dispenser may be used for transferring volumes of less than 100 mL, less than 10 mL, less than 5 mL, less than 100 μL, less than 10 μL, or less than 0.5 μL.

The device can further include a member for providing a droplet to a first spot (or feature) having a plurality of support-bound oligonucleotides. In some embodiments, the droplet can include one or more compositions comprising oligonucleotides (referred herein as nucleotide addition constructs) having a specific or predetermined nucleotide to be added and/or reagents that allow one or more of hybridizing, denaturing, chain extension reaction, ligation, and digestion, so as to produce a first nucleic acid product which includes the first nucleotide addition. In some embodiments, different compositions or different nucleotide addition constructs may be deposited at different addresses on the support during any one iteration so as to generate an array of predetermined oligonucleotide sequences (the different features of the support having different predetermined oligonucleotide sequences). One particularly useful way of depositing the compositions is by depositing one or more droplet, each droplet containing the desired reagent (e.g. nucleotide addition construct or partially double-stranded oligonucleotide comprising the desired nucleotide addition) from a pulse jet device spaced apart from the support surface, onto the support surface. Prior art pulse jet devices are available commercially for use in ink printing. The device may also include a member for advancing microfluidic communication from a first spot to a second spot on the support.

One skilled in the art will appreciate that DNA microarrays can have very high density of oligonucleotides on the surface (approximately $10^8$ molecules per feature), which can generate steric hindrance to polymerases needed for PCR or polymerase extension or to the ligase for ligation reactions. Theoretically, the oligonucleotides are generally spaced apart by about 2 nm to about 6 nm. For polymerases, a typical 6-subunit enzyme can have a diameter of about 12 nm. Therefore the support may need to be custom treated to address the surface density issue such that the spacing of surface-attached oligonucleotides can accommodate the physical dimension of the enzyme. For example, a subset of the oligonucleotides can be chemically or enzymatically cleaved, or physically removed from the microarray. Other methods can also be used to modify the oligonucleotides such that when primers are applied and annealed to the oligonucleotides, at least some 3' hydroxyl groups of the primers (start of DNA synthesis) are accessible by polymerase. The number of accessible 3' hydroxyl groups per spot can be stochastic or fixed. For example, the primers, once annealed, can be treated to remove some active 3' hydroxyl groups, leaving a stochastic number of 3' hydroxyl groups that can be subject to chain extension reactions. In another example, a large linker molecule (e.g., a concatamer) can be used such that one and only one start of synthesis is available per spot, or in a subset of the oligonucleotides per spot.

In some embodiments, a plurality of nucleotide acid constructs are provided at different features of the support. In some embodiments, the nucleic acid constructs (Nac) are partially double-stranded or duplex oligonucleotides. As used herein, the term "duplex" refers to a nucleic acid molecule that is at least partially double-stranded. Each of the plurality of partially double-stranded oligonucleotides comprises an oligonucleotide strand comprising an identical or a different predetermined sequence of X nucleotides, at least one predetermined nucleotide or nucleotide complementary to the predetermined nucleotide and a degenerate sequence of Y nucleotides. The terms "nucleoside" or "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. In various embodiments, within each feature on the solid support, each of the plurality of partially double-stranded oligonucleotides includes an identical predetermined subunit sequence of X nucleotides, at least one desired or predetermined nucleotide or a nucleotide complementary to the desired addition nucleotide and a degenerate sequence of Y nucleotides. In some embodiments, X is between 2 and 50. More particularly, X is between 3 and 20. In some examples, X is 3, 4, 5, 6, 7, 8, 9, or 10. In certain embodiments, Y is between 5 and 100. More particularly, Y is between 5 and 20, or Y is 5, 6, 7, 8, 9, 10, 11, 12, 13, 14, 15, 16, 17, 18, 19, or 20. In general, a sequence is called degenerate if some of its positions have several possible bases. Assuming= $\{T, C, A, G\}$ is the DNA alphabet, a sequence (e.g. a oligonucleotide) can be shown as S=$x_1 x_2 \ldots x_l$, where $x_i \subset \Sigma$, $x_i \neq \emptyset$ and l is the length of S. For example, in the oligonucleotide P*=$\{G\}\{G\}\{C,G\}\{A\}\{T,C,G\}\{A\}$ the third position is C or G and the fifth is C, T or G. The degeneracy of a sequence is the number of unique sequence combinations it contains, which can be calculated as d(S)=$\Pi_{i=1}^{l} |x_i|$. For example, d(P*)=1×1×2×1×3×1=6. In various embodiments, degenerate sequences can be used to improve the tolerance of the annealing reaction such that any given single-stranded oligonucleotide with a free 3'-OH group can bind to the degenerate binding sequence.

In some examples, the device has at least 100, 1,000, 4,000, 10,000, 100,000, 1,000,000 or more different features (or "regions" or "spots") at a particular location (i.e., an "address"). It should be appreciated that a device may comprise one or more solid supports. Depending upon the use, any or all of the arrays may be the same or different from one another and each may contain multiple spots or features.

In some embodiments, the duplex oligonucleotides or partially double-stranded oligonucleotides comprises a nucleotide addition construct sequence. In some embodiments, the nucleotide addition sequence comprises at its 5' end a degenerate single-stranded sequence. The nucleotide addition construct can be introduced at a first feature so as to hybridize to the anchor oligonucleotides through its 5' end binding sequence (e.g. degenerate sequence or specific binding sequence) thereby forming a first nucleic acid product: a anchor oligonucleotide-nucleotide addition construct hybrid. In some embodiments, the duplex oligonucleotide comprising a nucleotide addition construct is deposited at a feature or location using an ink jet device or a drop deposition from pulse jets device. As used herein the term "depositing" means to position, place a composition at a specific location on the surface to the support. Depositing includes contacting one composition with another. Depositing may be manual or automatic, e.g., "depositing" may be accomplished by automated robotic devices. A "pulse jet" refers to any device which can dispense drops of a fluid composition onto a support. Pulse jets operate by delivering a pulse of pressure (such as by a piezoelectric or thermoelectric element) to liquid adjacent an outlet or orifice such that a drop can be dispensed therefrom.

Figure 1:
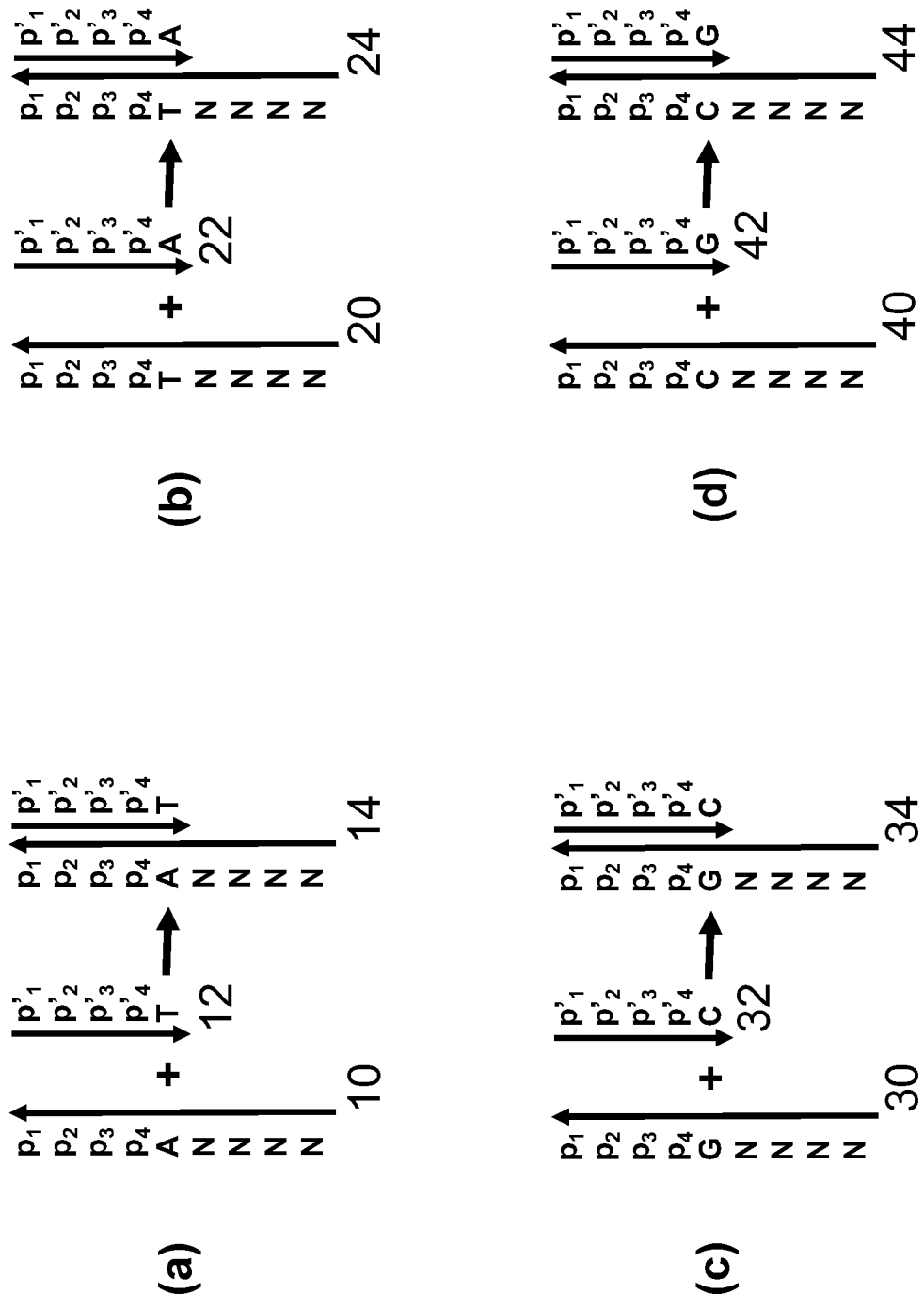
FIG. 1 is a non-limiting schematic illustration of an embodiment of a method for synthesizing nucleotide addition constructs.

FIG. 1 shows an exemplary method for producing nucleotide addition construct (also referred herein as construction duplexes or partially double-stranded oligonucleotides) which can hybridized and/or be ligated to an anchor oligonucleotide immobilized onto a solid support. In a preferred embodiment, the nucleotide addition constructs (Nac), comprise a first oligonucleotide hybridized to a second shorter construction oligonucleotide. In preferred embodiments, the nucleotide addition constructs can be ligated to the anchor oligonucleotides so as to confer a single or multiple nucleotide addition in subsequent process steps. In some embodiments, the first and second oligonucleotide sequences used to prepare the nucleic acid constructs may be synthetized by standard phosphoramidite synthesis. The degenerate nucleotide sequence can be are generated by synthesizing the degenerate base positions with a mixture of the corresponding nucleotide precursors. FIG. 1a shows an exemplary composition comprising a first oligonucleotide (10) comprising from the 5' end to the 3' end: a set of degenerate bases N followed by a single base which is complimentary to the desired addition nucleotide, in this case A, followed by a set of specific nucleotides (labeled $p_1$, $p_2$, $p_3$, $p_4$ etc. . . . ). A second, shorter construction oligonucleotide (12) is provided comprising starting from the 3' end: the desired addition nucleotide and a sequence ($p'_1$, $p'_2$, $p'_3$, $p'_4$ etc) which is complementary to the first nucleotide addition construct bases $p_1$, $p_2$, $p_3$, $p_4$. In preferred embodiments, the first oligonucleotide (10) and the second oligonucleotide (12) are selectively hybridized under appropriate hybridization conditions to form duplex (14) having a double-stranded portion comprising the complementary bases and a 5' (or 3') single-stranded portion. In some embodiments, the single-stranded portion or overhang comprises a plurality of degenerate bases. Yet, in other embodiments the single-stranded portion or overhang comprises a sequence that is complementary to the anchor or support-bound oligonucleotide. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. In some embodiments, the number of degenerate bases may be about 2, about 4, about 5 about 6 about 7 about 8 about 9 about 10, about 20, about 25, about 30, about 50. Referring to FIG. 1, construction duplex oligonucleotides are formed using a first oligonucleotide having a sequence comprising (from 5' to 3') about five degenerate bases at its 5' end, followed by a desired nucleotide addition (e.g. A, T, G, C, U), followed by a predefined sequence p1, p2, p3, p4. For example, the first oligonucleotide sequence (Nac) may be NNNA$p_4p_3p_2p_1$, NNNT$p_4p_3p_2p_1$, NNNC$p_4p_3p_2p_1$, or NNNG$p_4p_3p_2p_1$ as illustrated in FIG. 1 a-d. In FIG. 1b-d, similar preparations or compositions are provided for each of the four other possible nucleotide additions such that construct (14) is the nucleotide addition construct for T (NacT), construct (24) is the nucleotide addition construct for A (NacA), construct (34) is the nucleotide addition construct for C (NacC), and construct (44) is the nucleotide addition construct for G (NacG).

In some embodiments, a first oligonucleotide is hybridized through its degenerate bases to the support-bound oligonucleotide at a first feature on the solid support. In other preferred embodiment, a first oligonucleotide is hybridized to a second oligonucleotide having a sequence complementary to part of the first oligonucleotide sequences (e.g. T$p'_4p'_3p'_2p'_1$, A$p'_4p'_3p'_2p'_1$, C$p'_4p'_3p'_2p'_1$, G$p'_4p'_3p'_2p'_1$). In a preferred embodiment, the second oligonucleotide is shorter than the first oligonucleotide and hybridized to the 3' end of the first oligonucleotide.

In some embodiments, the bases $p_4p_3p_2p_1$ hybridized to their complementary bases p'4p'3p'2p'1 and form a restriction enzyme binding site. In another embodiment, the sequence p'4p'3p'2p'$_1$ etc. comprises one or more RNA bases. In a preferred embodiment, at least the nucleotide base closest to the specific addition base ($p'_4$) is an RNA base. In other embodiments, the sequence $p'_4p'_3p'_2p'_1$ etc. contains one or more uracil bases. In an exemplary embodiment, at least the nucleotide base closest to the specific addition base in the sequence of the second oligonucleotide ($p'_4$) is an uracil base.

In some embodiments, nucleotide addition constructs comprising a desired or predetermined dinucleotide sequence (16 different nucleic acid constructs), or a desired trinucleotide sequence (64 different nucleic acid constructs), or a desired tetranucleotide sequence (256 different nucleic acid constructs) etc. can be generated, added and hybridized to the plurality of support-bound oligonucleotides.

Figure 2:
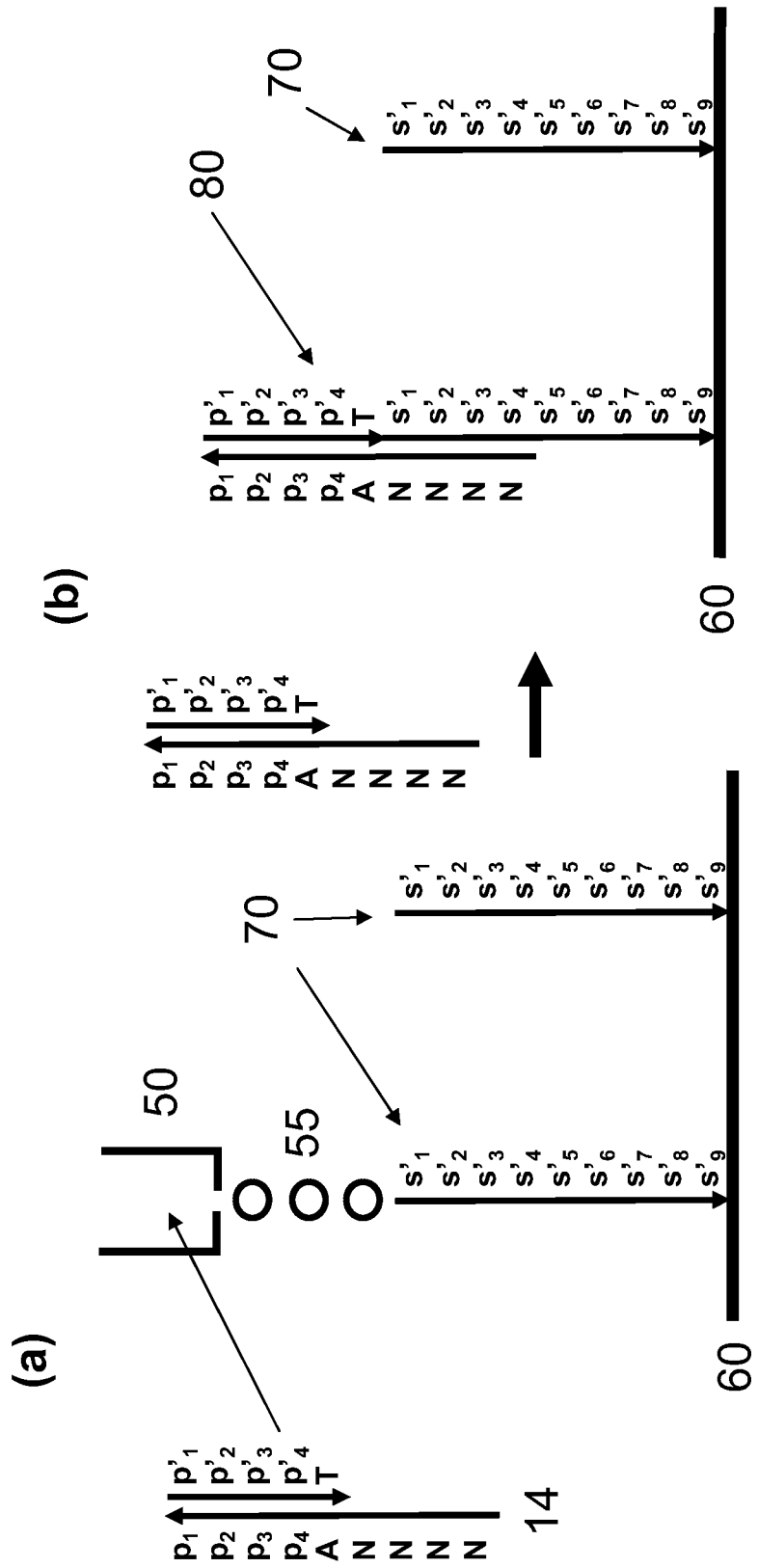
FIG. 2 is a non-limiting schematic illustration of an ink jet based deposition of nucleotide addition constructs at discrete features comprising support-bound oligonucleotides.
Figure 2:
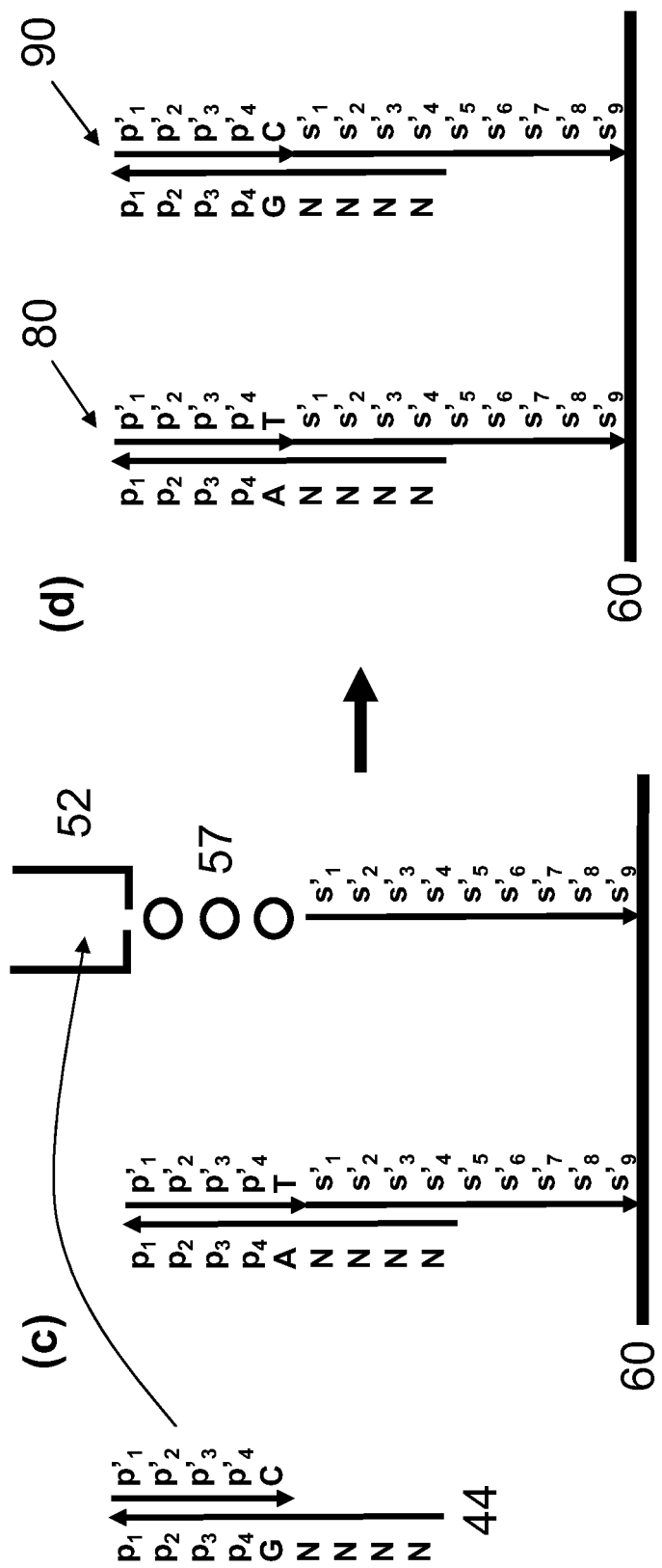

FIG. 2 shows an exemplary process for the addition nucleotide addition constructs at different features on a support. In an exemplary embodiment, an ink-jet based device is used for depositing specific nucleotide addition constructs (Nac) at specific locations (or features) on the surface of a support. Referring to FIG. 2(a), an ink jet device (50) may be loaded with a specific nucleotide addition construct (e.g. NacA, NacC, NacG, NacT). FIG. 2a illustrates an exemplary embodiment wherein NacT (14) is deposited within a droplet (55) onto a first feature on a support (60) using an ink jet device (50). The ink jet (50) may be programmed to fire one or more droplets (55) at specific locations or features of a surface (60) comprising support-bound oligonucleotides (70). According to preferred embodiments, the single-stranded degenerate regions of the nucleic acid constructs (also referred herein as construction duplex) are allowed to anneal to the single-stranded support-bound oligonucleotides (70) to form a nucleic acid construct-support-bound oligonucleotide hybrid (FIG. 2b, 80). Referring to FIG. 2c, a second ink jet head (52) is loaded with a second specific nucleotide addition construct, for example NacC (44). The ink jet (52) may be programmed to fire one or more droplets (57) at a second set of specific locations or features on the surface (60) to bind to the support-bound oligonucleotides immobilized at that location thereby to form a nucleic acid construct-support-bound oligonucleotide hybrid (90). One would appreciate that a limitation on the number of bases that can be added at one time may depend on the number of inkjet heads that can be used. In some embodiments, sixty-four ink jets heads may be used to allow for the addition of 3 bases at a time.

Figure 3:
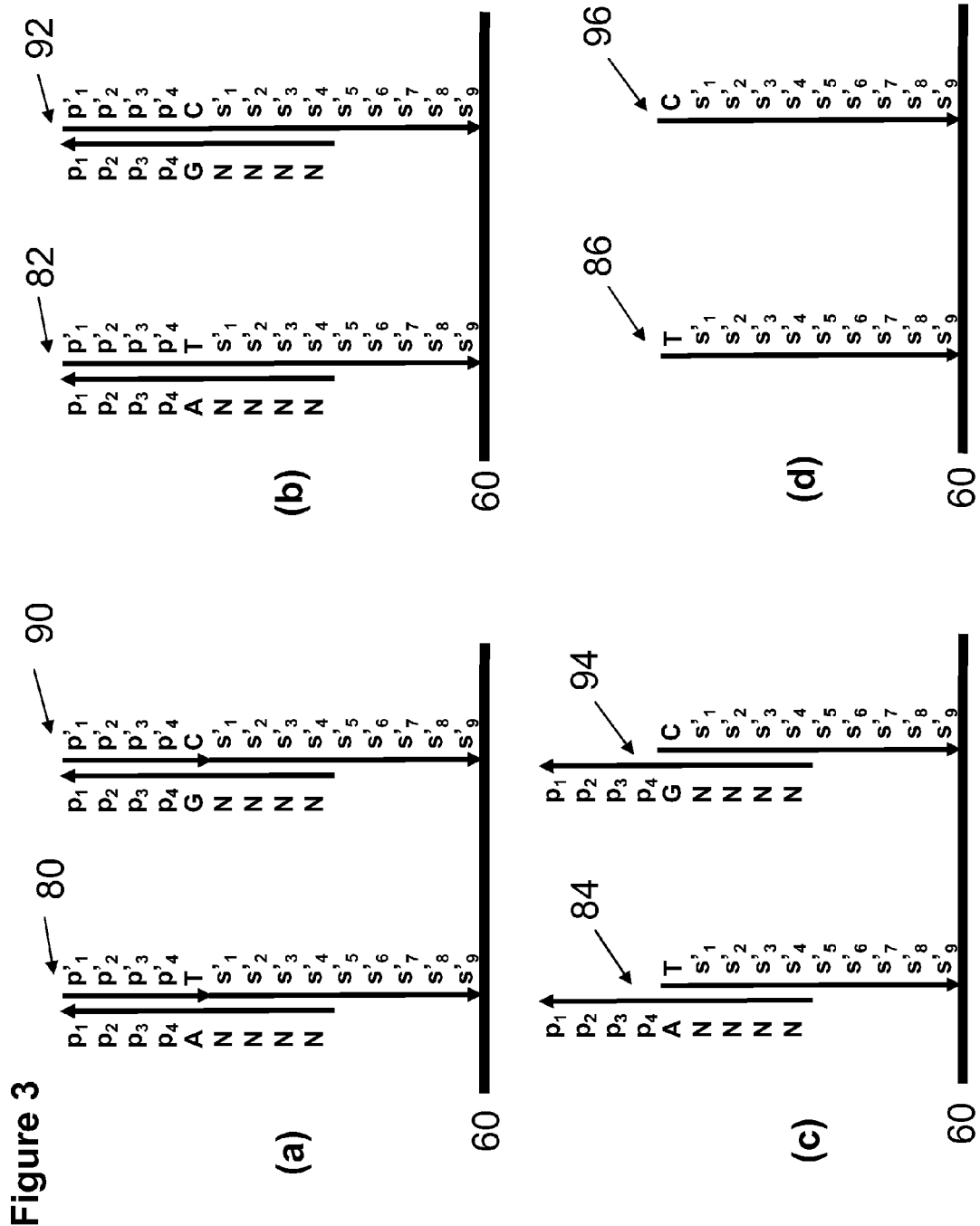
FIG. 3 is a non-limiting schematic illustration of the process of single nucleotide addition to support-bound oligonucleotides by hybridization of nucleotide addition constructs to support-bound oligonucleotides and removal of unwanted sequences.
Figure 4:
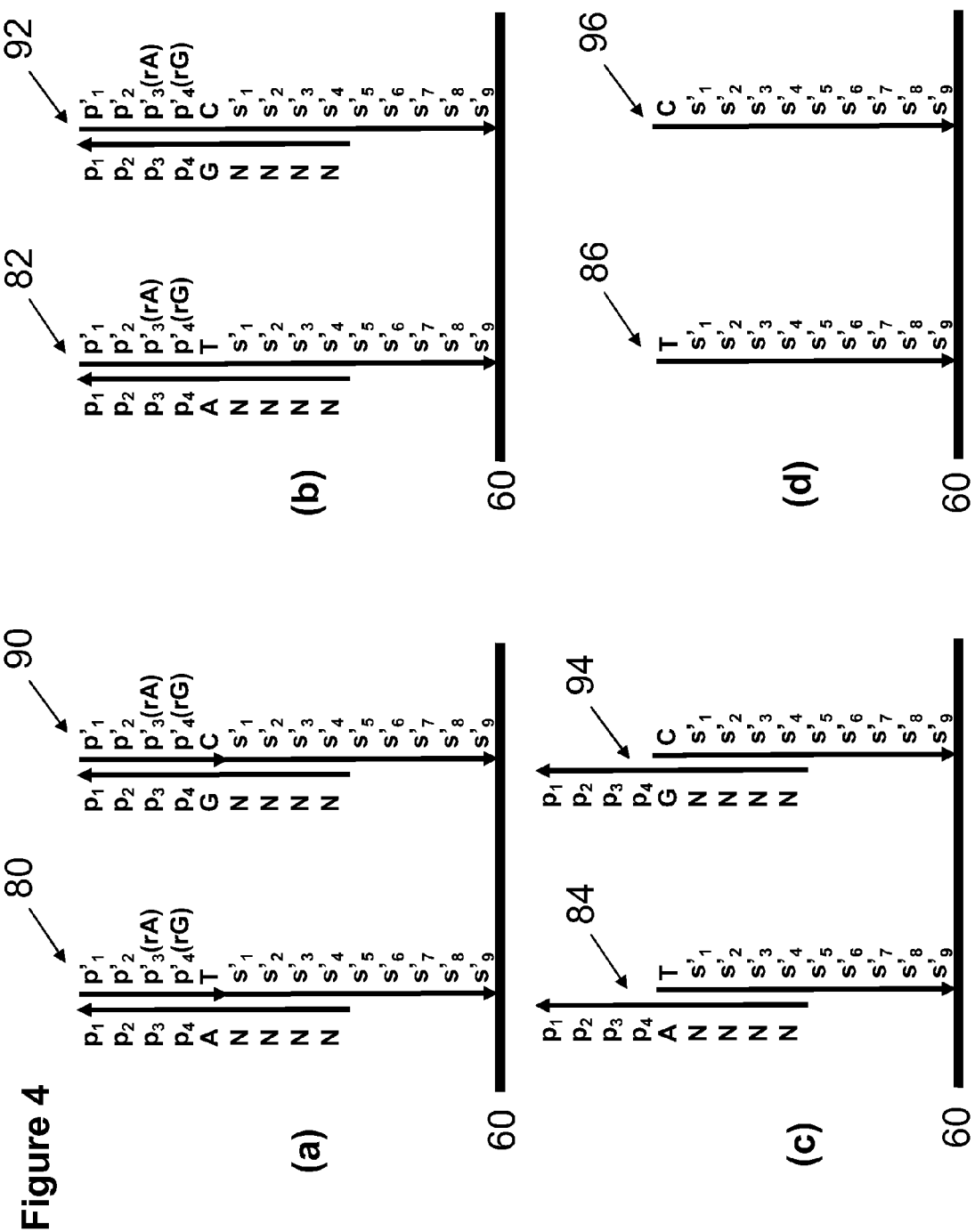
FIG. 4 is a non-limiting schematic illustration of the process of single nucleotide addition to support-bound oligonucleotides by hybridization of nucleotide addition constructs to support-bound oligonucleotides followed by a RNAse degradation step.

FIG. 3 shows an exemplary process to generate the addition of a single nucleotide to an anchor or support-bound oligonucleotide. In some embodiment, after formation of a nucleic acid construct-support-bound oligonucleotide hybrid, at least a portion of the nucleic acid construct-support-bound oligonucleotide hybrid is degraded to expose the nucleotide addition at the 5' end of the anchor oligonucleotide. As illustrated in FIG. 3 and FIG. 4, the surface of the solid support comprises a plurality of different nucleotide addition constructs hybridized to a plurality of support-bound oligonucleotides at a plurality of different locations on surface 60. In an exemplary embodiment, bases $p'_1, p'_2, p'_3$ etc. contain at least one RNA base. In a preferred embodiment, at least the nucleotide closest to the specific addition nucleotide (in this example downstream of $p'_4$) is an RNA base. FIG. 3a illustrates a NacT—support-bound oligonucleotide hybrid (80) and a NacC-support-bound oligonucleotide hybrid (90) bound at specific locations or features on surface (60). In a subsequent step, and referring to FIG. 3b and FIG. 4b, a ligase (for example a high temperature ligase) is provided under conditions promoting the ligation of the 3' end of the nucleic acid construct to the support-bound oligonucleotide. By ligation is meant any method of joining two or more nucleotides to each other. Ligation can include chemical or enzymatic ligation, including DNA ligase I, DNA ligase II, DNA ligase III, DNA ligase IV, E. Coli DNA ligase, T4 DNA ligase, T4 RNA ligase 1, T4 RNA ligase 2, T7 ligase, T3 DNA ligase, thermostable ligase (taq ligase) and the like. In some embodiments, a ribonuclease (for example an RNase) or alkaline phosphatase is added to degrade said bases $p'_1, p'_2$ etc. Any small number of bases (84, 94) which remain hybridized to the elongated product (86, 96) may be melted off and washed away. FIG. 4d illustrates the resulting elongated product comprising the anchor oligonucleotides, including the desired (predetermined) single nucleotide additions (for example T, (86) and C, (96)). One would appreciate that the step of hybridizing a duplex construction oligonucleotide to the support-bound oligonucleotide immobilized to the support, ligating the duplex construction oligonucleotide to the anchor oligonucleotide, degrading at least a portion of the duplex construction oligonucleotide (for example, using a RNase) can be repeated so as to yield nucleic acids of a desired length and predetermined sequence.

Figure 5:
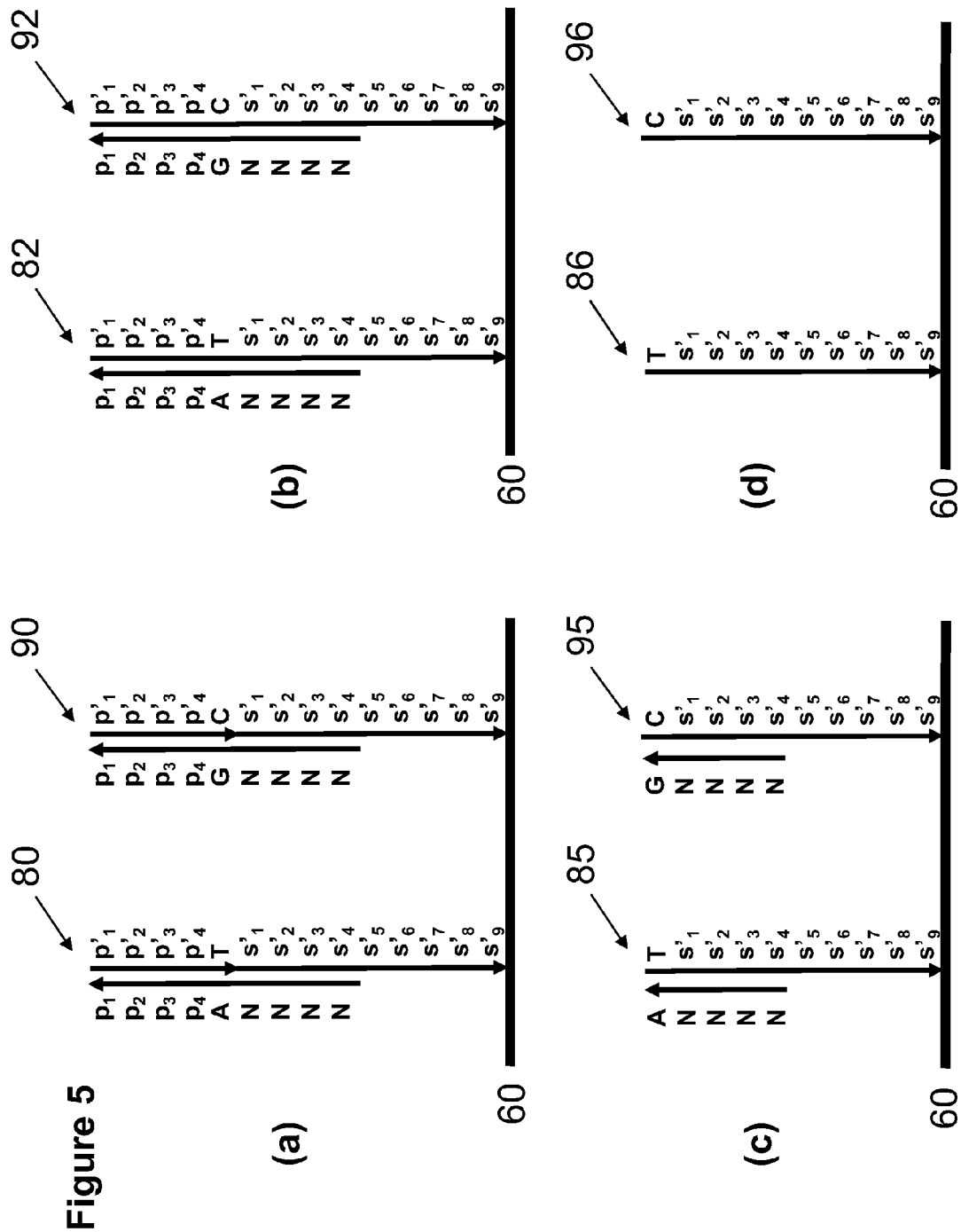
FIG. 5 is a non-limiting schematic illustration of the process of single nucleotide addition to support-bound oligonucleotides by hybridization of nucleotide addition constructs to support-bound oligonucleotides and removal of the unwanted sequences by cleavage.
Figure 6:
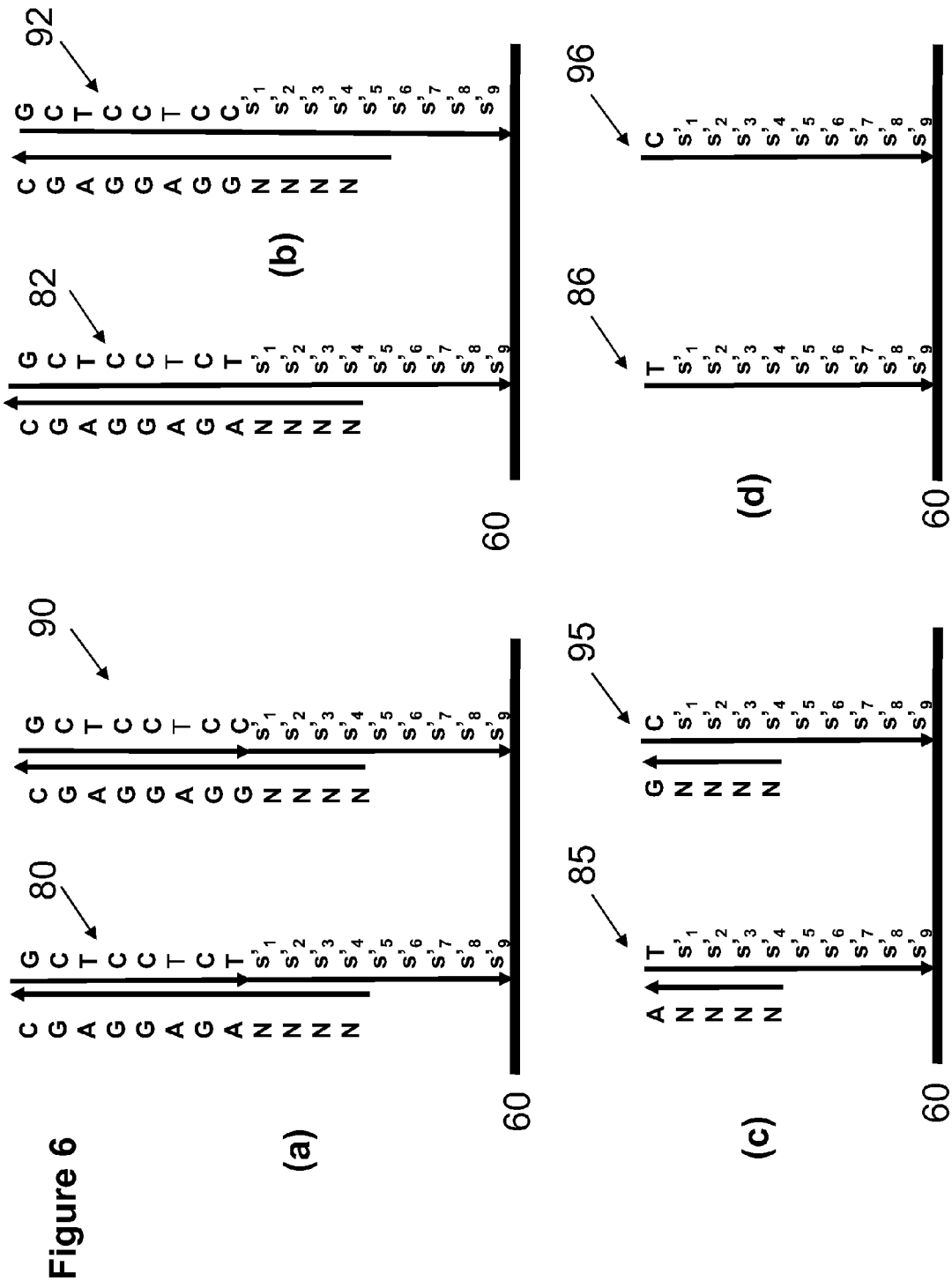
FIG. 6 is a non-limiting schematic illustration of the process of single nucleotide addition to support-bound oligonucleotides by hybridization of nucleotide addition constructs NacT (80) and NacC (90) to support-bound oligonucleotides and removal of the unwanted sequences by cleavage using a restriction endonuclease. The partially double-stranded Nucleotide addition construct NacT has the following sequence:
5' NNNNAGAGGAGC 3' (SEQ ID NO: 1)
3' TCTCCTCG 5'

In other aspect of the invention, the double-stranded portion of the nucleotide addition constructs (bases p1, p2, p3 etc. hybridized to their complementary bases $p'_1, p'_2, p'_3$ etc) are designed to provide the sequence corresponding to the binding site for a restriction enzyme. FIG. 5 and FIG. 6 illustrate an exemplary embodiment wherein NacT—support-bound oligonucleotide hybrid (80) and a NacC-support-bound oligonucleotide hybrid (90) are immobilized at specific locations or features on surface (60). As described above, and referring to FIG. 5b and FIG. 6b, a ligase (for example, a high temperature ligase) is provided at the specific features under conditions promoting the ligation of the 3' end of the Nac to the support-bound oligonucleotide, thereby forming a duplex oligonucleotide (82, 92). In some embodiments, the duplex oligonucleotide comprises a binding site for a restriction enzyme. In a subsequent step, an appropriate restriction enzyme, is provided under the appropriate conditions to promote a double-strand cut. In a preferred embodiment, the restriction enzyme is a type II endonuclease capable of cleaving the double-stranded sequence just above the desired nucleotide addition thereby forming a product comprising the support-bound oligonucleotide hybrid with a single base addition (FIG. 6, 85 and 95). Accordingly, the elongated support-bound oligonucleotide comprises a single nucleotide addition. One would appreciate that depending on the cleavage site, the elongated support-bound oligonucleotide may comprise 2, 3, 4 or more desired nucleotides addition. In some embodiments, the endonuclease is BspQI or BsaI. The term "type-IIs restriction endonuclease" refers to a restriction endonuclease having a non-palindromic recognition sequence and a cleavage site that occurs outside of the recognition site (e.g., from 0 to about 20 nucleotides distal to the recognition site). Type IIs restriction endonucleases may create a nick in a double-stranded nucleic acid molecule or may create a double-stranded break that produces either blunt or sticky ends (e.g., either 5' or 3' overhangs). Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco311, Esp3 I, Aar I; and enzymes that produce a blunt end, such as, for example, Mly I and Btr I. Type-IIs endonucleases are commercially available and are well known in the art (New England Biolabs, Beverly, Mass.).

In some embodiments, and referring to FIG. 5c-d and FIG. 6c-d, the sequence that remain hybridized to the product (85 and 86) may be melted off and washed off the feature thereby producing the support-bound oligonucleotides having desired or predetermined single base additions (86 and 96). These steps may be repeated to add a plurality of nucleotides and until the target oligonucleotide having the predefined sequence is produced.

In some embodiments, and referring to FIG. 7, the sequence $p'_1, p'_2, p'_3$ of the partially double-stranded oligonucleotide may contain at least one uracil base. In a preferred embodiment, the nucleotide base the closest to the desired nucleotide addition (for example $p'_4$ in FIG. 7) is a uracil base. Referring to FIG. 7a, a NacT-anchor oligonucleotide hybrid (80) and a NacC-anchor oligonucleotide hybrid (90) are resident (e.g. immobilized) at specific locations on surface 60. Referring to FIG. 7b, a ligase (e.g. high temperature ligase) is provided under conditions promoting the ligation of the 3' end of the nucleotide addition construct to the support-bound oligonucleotide. In FIG. 7c, a mixture of uracil DNA glycosylase (UDG) and endonuclease VIII (from Enzymatics®) is added to the composition containing a uracil-containing oligonucleotide sequence. UDG can catalyze the excision of the uracil base, creating an abasic site with an intact phosphodiester backbone while the lyase activity of endonuclease VIII breaks the phosphodiester backbone at both the 3' and the 5' sides of the abasic site separating the synthesis nucleotide(s) from the carrier oligonucleotide. In a subsequent step, unwanted nucleotides may be melted off and washed off thereby producing an elongated anchor or support-bound oligonucleotide. In some embodiments, the elongated support-bound oligonucleotide comprises a single base addition (FIG. 7, 86 and 96). Yet, in other embodiments, the elongated support-bound oligonucleotide comprises a dinucleotide, a trinucleotide etc. . . . addition. These steps may be repeated to allow the synthesis of the nucleic acids (e.g. oligonucleotides) having the predefined sequence and length.

Aspect of the invention relates to high fidelity in situ oligonucleotide synthesis. Devices and methods to selectively isolate the correct nucleic acid sequence from the incorrect nucleic acid sequences are provided herein. One should appreciate that the combined repetitive yield of the ligation and digestion/degradation steps may limit the ultimate length of the oligonucleotide to be synthesized. For instance, it is possible that the nucleotide addition construct fails to hybridize to the support-bound oligonucleotide, or that the nucleotide addition construct fails to ligate to the support-bound oligonucleotide or that the resulting nucleotide addition construct-support-bound oligonucleotide hybrid is not properly digested or cleaved, leading to an error-containing oligonucleotide such as an oligonucleotide including a deletion or an addition in the intended synthesized strand. Accordingly, some embodiments relate to the removal of oligonucleotides from the synthesis process if the nucleotide addition constructs (Nac) fails to hybridize and/or to be ligated to the support-bound oligonucleotide. In some embodiments, after every ligation step, the surface may be treated with alkaline phosphatase. One would appreciate that oligonucleotides that were successfully ligated will have a phosphate at their 5' end. The 5' end phosphate can be removed with impunity. However, one skilled in the art would appreciate that the support-bound oligonucleotides which failed to hybridize and/or ligate with nucleotide addition constructs will lose its 5' phosphate and will no longer be available to undergo ligation. This can prevent these support-bound oligonucleotides from further participating in the synthesis process thereby preventing the synthesis of error-containing nucleic acid sequences.

One would appreciate that if nucleotide addition construct-anchor oligonucleotide hybrid is not properly digested or cleaved, a sequence error such as a deletion may be introduced. For example, incomplete cleavage in one round of synthesis can prevent nucleotide addition in a next round and successful addition in a next round would yield to a product sequence comprising a base pair deletion. In some embodiments, alternating the use of restriction enzyme specificity during the synthesis process may serve as a blocking agent. In some embodiments, a first restriction enzyme can be used after a first addition (e.g. after ligation of a first nucleotide addition construct) and a second restriction enzyme can be used after a second addition (e.g. after ligation of a second nucleotide addition construct), each restriction enzyme having a sequence specificity. The ligation products will be cleaved by the restriction enzyme only if the contain the appropriate sequence.

In some embodiments, a set of labeled nucleotide addition constructs (Nac) consisting for example of NacT (140), NacA (150), NacC (160) and NacG (170) are produced (FIG. 8). In certain exemplary embodiments, a detectable label can be used to detect one or more nucleotides and/or oligonucleotides described herein. Examples of detectable markers include various radioactive moieties, enzymes, prosthetic groups, fluorescent markers, luminescent markers, bioluminescent markers, metal particles, protein-protein binding pairs, protein-antibody binding pairs and the like. In some embodiments, a fluorescent label such as a fluorophore or a chemiluminescent label is associated or attached to the nucleotide addition construct. Examples of fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorimidases, phosphatases, peroxidases, cholinesterases and the like. Identifiable markers also include radioactive compounds such as $^{125}I$, $^{35}S$, $^{14}C$, or $^{3}H$. Identifiable markers are commercially available from a variety of sources. Preferably the oligonucleotide probes or nucleotides are fluorescently labeled with four different fluorophores, each fluorophore being associated to a particular base or nucleotide.

Some aspects of the invention relate to the analysis, detection and characterization of the newly synthesized oligonucleotides using an analysis device. In some embodiments, the analysis device uses a CCD (or CMOS) optical sensor to allow rapid imaging of the array. Surface-bound fluorescent labels from the array fluoresce in response to the light. In some embodiments, the fluorescent constructs are employed in combination with CCD imaging systems. In some embodiments, the imaging system allows the detection and/or measurement of labeled molecules, and/or localization of the fluorescent signal. A computer can transform the data into another format for presentation. The resulting data can be displayed as an image with color in each region varying according to the light emission.

In an exemplary embodiment, an ink jet (50) is loaded with a specific nucleotide addition constructs, for example fluorophore labeled NacT 140 (FIG. 8*a*) Ink jet (50) may be programmed to fire one or more droplets (55) at specific locations of a surface (65) which comprises anchor oligonucleotides (70). In some preferred embodiments, the density of anchor oligonucleotides at each feature is about one anchor oligonucleotide per optically resolvable surface a real patch.

FIG. 8*c* illustrates the use of an ink jet to deposit labeled nucleotide addition constructs to features comprising support-bound oligonucleotides to form a Nac—support-bound oligonucleotide hybrid (180). To confirm that the formation of the labeled Nac—support-bound oligonucleotide hybrid, the fluorophore labeled Nac may be excited such that it emits a photon (200) which may be detected by a detector (210). In some embodiments, the detector (210) is a fluorescent array detector such as a CCD (or CMOS) imaging system which enables the imaging of a specific a region of the support's surface or the entire surface in parallel. If no fluorescence signal is detected, it is an indication that nucleotide addition construct coupling to the anchor oligonucleotide did not take place and the ink-jet can then be directed to deposit a nucleotide addition construct an additional time. Conversely, the same system may be used to confirm proper nucleotide addition construct digestion or cleavage by observing the disappearance of fluorescence signal after the digestion or cleavage step. Additional steps may be taken to confirm proper ligation by constructing a nucleotide addition construct that has two separate fluorophores, one on the 3' up strand (e.g. upper strand) and one on the 5' up strand (e.g. lower strand), for example, each of different colors. In some embodiments, the hybridization of the initial nucleotide addition construct to support-bound oligonucleotide can be confirmed by fluorescently observing the presence of both fluorophores. In some embodiments, the ligase can be added and the 3' up strand of the nucleotide addition construct can be melted off. If proper ligation has taken place, one will observe the disappearance of the 3' up fluorophore but not of the 5' up fluorophore. The 3' up oligonucleotide may then be re-hybridized and followed by either restriction enzyme cleavage or endonuclease digestion as discussed above (FIGS. 5 and 6). After restriction enzyme cleavage or endonuclease digestion followed by melting, the fluorescent signal from both fluorophores should disappear. One would appreciate that aspects of the invention provide specific feedback or readouts for the different step in the oligonucleotide synthesis such as i) hybridization of the nucleotide addition construct to the anchor oligonucleotide, ii) proper ligation to the anchor oligonucleotide iii) cleavage of the unwanted portion of the nucleotide addition construct. In some embodiments, in order to confer a high effective repetitive yield for such in-situ nucleic acid synthesis, hybridization, ligation or cleavage/digestion may be repeated upon failure of any of the feedback readouts detailed above.

In some embodiments, the oligonucleotides are used for assembling a target polynucleotide having a predefined sequence. In some embodiments, the target polynucleotide may be assembled using an assembly procedure that may include several parallel and/or sequential reaction steps in which a plurality of different nucleic acids or oligonucleotides are synthesized or immobilized, amplified, and are combined in order to be assembled (e.g., by extension or ligation) to generate a longer nucleic acid product to be used for further assembly, cloning, or other applications (see U.S. provisional application 61/235,677 and PCT application PCT/US09/55267 which are incorporate herein by reference in their entirety).

The present invention provides among other things novel methods and devices for synthesis of nucleic acids. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

We claim:

1. A method for synthesizing a nucleic acid having a predefined sequence, the method comprising:
    a) providing a support comprising a plurality of features, each feature comprising a plurality of single-stranded support-bound oligonucleotides;
    b) hybridizing a partially double-stranded first oligonucleotide to at least a first support-bound oligonucleotide at a first feature, wherein the first partially double-stranded oligonucleotide comprises a 5' overhang and a ligatable predetermined addition nucleotide at a 3' end of the double-stranded portion;
    c) ligating the partially double-stranded first oligonucleotide to the first support-bound oligonucleotide thereby generating a first ligation product comprising the predetermined addition nucleotide; and
    d) cleaving the first ligation product thereby generating a first elongated support-bound oligonucleotide comprising the predetermined addition nucleotide.

2. The method of claim 1 wherein in the step of providing the at least first oligonucleotide is in solution within a droplet and is deposited at the first feature.

3. The method of claim 1 further comprising repeating steps b), c) and d) thereby providing the nucleic acid having the predefined sequence.

4. The method of claim 1 wherein in the step of hybridizing the partially double-stranded oligonucleotide comprises a double-stranded portion and a single-stranded 5' overhang, wherein the single-stranded overhang comprises degenerate bases.

5. The method of claim 1 wherein the partially double-stranded oligonucleotide having a 5' overhang is generated by hybridizing a first single-stranded construction oligonucleotide comprising at its 5' end a predefined sequence and at its 3' end the predetermined ligatable addition nucleotide to a longer single-stranded oligonucleotide comprising at its 3' end a sequence complementary to the 5' end predefined sequence of the first construction oligonucleotide and comprising a nucleotide complementary to the predetermined ligatable addition nucleotide upstream to the 3' end sequence.

6. The method of claim 5 wherein the first construction oligonucleotide further comprises RNA base upstream of the predetermined addition nucleotide.

7. The method of claim 1 wherein the 5' overhang of the partially double-stranded oligonucleotide is complementary to the 5' end of the support-bound oligonucleotide.

8. The method of claim 1 wherein the step of cleaving comprises cleaving the first ligated product using a RNase.

9. The method of claim 1 wherein in the step of hybridizing the double-stranded portion of the partially double-stranded oligonucleotide comprises a restriction endonuclease binding site.

10. The method of claim 9 wherein the restriction endonuclease binding site is a type IIS endonuclease binding site.

11. The method of claim 1 wherein in the step of cleaving the ligation product is cleaved with a restriction enzyme.

12. The method of claim 11 wherein cleavage of the ligation product provides an elongated support-bound oligonucleotide comprising one or more predetermined addition nucleotides.

13. The method of claim 1 further comprising melting off nucleotides from the elongated support-bound oligonucleotide.

14. The method of claim 1 wherein in the step of hybridizing the partially double-stranded oligonucleotides comprise a detectable label.

15. The method of claim 14 wherein the label is a fluorescent label.

16. The method of claim 14 further comprising analyzing the hybridization step and/or the ligation step and wherein the presence of the detectable label is indicative of the completion of the steps.

17. The method of claim 16 wherein the steps of analyzing are performed using an imaging system.

18. The method of claim 17 wherein the imaging system is a CCD.

19. The method of claim 14 further comprising analyzing the cleaving step and wherein the absence of detectable label is indicative of the completion of the step.

20. The method of claim 1 further comprising depositing the partially double-stranded first oligonucleotide at the first feature using an ink jet device.

21. The method of claim 1 wherein in the step of hybridizing a plurality of partially double-stranded oligonucleotides are provided at a plurality of different features of the support.

22. The method of claim 21 wherein the plurality of partially double-stranded oligonucleotides comprises a 5' single-stranded overhang, a predetermined addition nucleotide and a double-stranded sequence and wherein the double-stranded sequence is identical within the plurality of partially double-stranded oligonucleotides.

23. The method of claim 22 wherein the oligonucleotides of the plurality of partially double-stranded oligonucleotides differ only with at least one predetermined nucleotide addition.

24. The method of claim 23 wherein the predetermined nucleotide addition is A, T, G or C.

25. The method of claim 1 wherein the first elongated support-bound oligonucleotide comprises one or more predetermined addition nucleotides.

26. The method of claim 1 wherein the predetermined nucleotide addition is A, T, G or C.

* * * * *

SEQUENCE LISTING

```
<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: n is A, or G, or C or T

<400> SEQUENCE: 1
nnnnagagga gc                                                        12

<210> SEQ ID NO 2
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: n is A, or G, or C or T

<400> SEQUENCE: 2
nnnnggagga gc                                                        12
```